United States Patent
Ying et al.

(10) Patent No.: US 8,343,443 B2
(45) Date of Patent: Jan. 1, 2013

(54) FLUID PROCESSING AND TRANSFER USING INTER-CONNECTED MULTI-CHAMBER DEVICE

(75) Inventors: Jackie Y. Ying, Singapore (SG); Guolin Xu, Singapore (SG); Hock Ming Jeremy Loh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 214 days.

(21) Appl. No.: 12/935,576

(22) PCT Filed: Jun. 23, 2008

(86) PCT No.: PCT/SG2008/000222
§ 371 (c)(1), (2), (4) Date: Sep. 29, 2010

(87) PCT Pub. No.: WO2009/123565
PCT Pub. Date: Oct. 8, 2009

(65) Prior Publication Data
US 2011/0030809 A1 Feb. 10, 2011

Related U.S. Application Data

(60) Provisional application No. 61/064,871, filed on Mar. 31, 2008.

(51) Int. Cl.
G01N 15/06 (2006.01)
G01N 33/00 (2006.01)
G01N 33/48 (2006.01)

(52) U.S. Cl. ....... 422/503; 422/68.1; 422/502; 422/504; 422/509; 436/43; 436/180

(58) Field of Classification Search .................... 422/50, 422/68.1, 502, 503, 504, 509; 436/43, 180
See application file for complete search history.

(56) References Cited

U.S. PATENT DOCUMENTS

| 5,994,056 A | 11/1999 | Higuchi |
| 6,025,114 A | 2/2000 | Popat et al. |
| 6,068,751 A | 5/2000 | Neukermans |

(Continued)

FOREIGN PATENT DOCUMENTS

CN 1272919 A 11/2000

(Continued)

OTHER PUBLICATIONS

Lee et al., "Microchip-based one step DNA extraction and real-time PCR in one chamber for rapid pathogen identification", Lab Chip, 2006, vol. 6, pp. 886-895.

(Continued)

*Primary Examiner* — Brian J Sines
(74) *Attorney, Agent, or Firm* — Klarquist Sparkman, LLP

(57) ABSTRACT

A micro-fluidic device comprises a body. The body defines pneumatic ports, chambers for receiving liquids, and a connecting conduit. Each port is sealed with a seal and is shaped to couple to a pneumatic conduit through the seal. At least some of the chambers each have a top opening and a bottom opening. The top openings are in fluid communication with corresponding ports. The bottom openings are in fluid communication with one another through the connecting conduit, which is above the bottom openings. Selective application of pneumatic pressures to the chambers through the pneumatic conduits can transfer a liquid from one chamber to another through the connecting conduit, for example, for processing bio-samples within the device.

32 Claims, 11 Drawing Sheets

U.S. PATENT DOCUMENTS

| | | |
|---|---|---|
| 6,167,910 B1 | 1/2001 | Chow |
| 6,168,948 B1 | 1/2001 | Anderson et al. |
| 6,171,785 B1 | 1/2001 | Higuchi |
| 6,374,684 B1 | 4/2002 | Dority |
| 6,664,104 B2 | 12/2003 | Pourahmadi et al. |
| 6,783,736 B1 | 8/2004 | Taylor et al. |
| 6,814,934 B1 | 11/2004 | Higuchi |
| 6,818,185 B1 | 11/2004 | Petersen et al. |
| 2004/0053403 A1 | 3/2004 | Jedrzejewski et al. |
| 2005/0148091 A1 | 7/2005 | Kitaguchi et al. |

FOREIGN PATENT DOCUMENTS

| | | |
|---|---|---|
| CN | 1370278 A | 9/2002 |
| CN | 1444646 A | 9/2003 |
| CN | 1556922 A | 12/2004 |
| EP | 0200362 A2 | 12/1986 |
| EP | 0487218 A1 | 5/1992 |
| EP | 0512334 B1 | 9/1999 |
| EP | 1203959 A1 | 5/2002 |
| EP | 0872562 B1 | 9/2002 |
| EP | 1878496 A1 | 1/2008 |
| JP | 2004-101292 | 4/2004 |
| WO | 99/67646 | 12/1999 |
| WO | 01/11374 A2 | 2/2001 |
| WO | 2005/033712 A1 | 4/2005 |
| WO | 2006/085948 A2 | 8/2006 |

OTHER PUBLICATIONS

International Search Report and Written Opinion, mailed Jan. 19, 2009, in related PCT patent application No. PCT/SG2008/000425.

International Preliminary Report on Patentability, mailed Jun. 17, 2010, in related PCT patent application No. PCT/SG2008/000425.

Yeung et al., "A DNA biochip for on-the-spot multiplexed pathogen identification", Neucleic Acids Research, 2006, vol. 34, p. e118.

International Search Report and Written Opinion, mailed Sep. 19, 2008, in related PCT patent application No. PCT/SG2008/000222.

International Preliminary Report on Patentability, dated Oct. 5, 2010, in related PCT patent application No. PCT/SG2008/000222.

Liu et al., "Fully integrated microfluidic biochips for DNA analysis", International Journal of Computational Engineering Science, 2003, vol. 4, p. 145-150.

Mei Liu, The State Intellectual Property Office of the People's Republic of China, "Notification of the First Office Action", Oct. 18, 2012, in related Chinese patent application No. 200880129491.2.

FLUID PROCESSING AND TRANSFER USING INTER-CONNECTED MULTI-CHAMBER DEVICE

CROSS-REFERENCE TO RELATED APPLICATION

This is the National Stage of International Application No. PCT/SG2008/000222, filed Jun. 23, 2008, which claims the benefits of U.S. provisional application No. 61/064,871, filed Mar. 31, 2008, the contents of which are incorporated herein by reference.

FIELD OF THE INVENTION

The present invention relates to fluid processing, more particularly to fluid processing and transfer using inter-connected multi-chamber devices.

BACKGROUND OF THE INVENTION

Preparation of biological samples, such as DNA, RNA, mRNA and protein from clinical samples in the forms of solids and fluids, may involve a series of processing steps, such as tissue dissociation, cell separation, cell lysis, gene extraction, and/or washing. This sometimes requires complex fluidic delivery and processing protocols. In some conventional processing methods, samples and reagents are contained and manually transferred using test tubes and micropipettes. This is time-consuming, labor-intensive, and prone to human error. There is also a significant risk of cross-contamination of nucleic acids between different samples. Some of the manual steps and operations may be automated using robotic systems, but the robotic systems are difficult to use for handling small amounts of samples. Moreover, automation typically requires added costs and expensive equipments.

A chip-based or cartridge-based micro-system can process a small amount of sample fluid within a closed fluidic system, thereby reducing risks of cross-contamination. Typically, the fluid flow within the chip- or cartridge-based systems is driven and regulated using pumps and valves. These systems have complex structures and low reliability, and are expensive and inconvenient to use.

SUMMARY OF THE INVENTION

According to an aspect of the present invention, there is provided a micro-fluidic device comprising a body. The body defines first, second and third pneumatic ports; first, second and third chambers; and a connecting conduit. Each of the ports is sealed with a seal and shaped to couple to a pneumatic conduit through said seal. Each of the chambers is for receiving a liquid, and has a top opening and a bottom opening. The top opening of each chamber is in fluid communication with a respective port. The connecting conduit is above each one of the bottom openings. The bottom openings are in fluid communication with one another through the connecting conduit. Selective application of pneumatic pressures to the chambers through said pneumatic conduits can transfer a liquid from one of said chambers to another one of said chambers through said connecting conduit. Each one of said chambers may have a bottom surface sloped downwardly towards said bottom opening of said each chamber. At least a section of said connecting conduit may be at a level above a liquid level in said chambers. The body may include a top portion, a bottom portion, and a middle portion. The chambers and connecting conduit may be defined by said middle and top portions. At least a section of said connecting conduit may be adjacent said top portion. The top openings of said chambers may be adjacent said top portion. The ports may be defined by said bottom portion. The middle portion may define conduits each extending between one of the ports and its corresponding top opening. The middle portion may define conduits each extending between one of the bottom openings and the connecting conduit. The top, middle and bottom portions may be separate portions, and the middle portion may be sandwiched between said top and bottom portions. At least one of said top and bottom portions may be formed of a flat sheet. At least one of said top portion and said bottom portion may be made of a plastic material. The body may define more than three inter-connected chambers, such as six to eleven inter-connected chambers. The liquid in a chamber may comprise a reagent, a buffer, a sample, or a gene binding conditioner. At least two chambers may contain different liquids. At least a portion of said body may be made of a polymer. The polymer may comprise polycarbonate or poly(methyl methacrylate). The seal may be made of a plastic material. The body may define a gene extractor chamber. The gene extractor chamber may contain a gene extractor and may be in fluid communication with said connecting conduit. The body may define a product chamber and a waste chamber, each in fluid communication with said gene extractor chamber. The device may be a cartridge. The pneumatic conduit may comprise a needle.

In accordance with another aspect of the present invention, there is provided an apparatus comprising a device as described in the preceding paragraph, and a station connectable to said device for selectively applying pneumatic pressures to said chambers through said ports of said device. The station may comprise a base configured for coupling with said device, a plurality of pneumatic conduits mounted on said base, shaped to couple to said ports through said seals when said device is coupled to said base, and a plurality of valves each connected to one of said pneumatic conduits for selectively regulating a fluid flow through said pneumatic conduits. A first set of the valves may be connected to a first pressure device for selectively applying to said ports a first pneumatic pressure, and a second set of the valves may be connected to a second pressure device selectively applying to said ports a second pneumatic pressure lower than said first pneumatic pressure. The first pneumatic pressure may be higher than one atmosphere, and the second pneumatic pressure may be lower than one atmosphere. The first pressure device may comprise a pressure pump, and said second pressure device may comprise a vacuum pump. The station may comprise a controller for controlling operation of said valves and said pressure devices. The station may comprise a computer in communication with said controller for controlling operation of said controller.

In accordance with a further aspect of the present invention, there is provided a method of operating the device described in the two preceding paragraphs, wherein at least one of the chambers contains a liquid. The method comprises coupling said pneumatic conduits to said ports; selectively applying different pneumatic pressures to said chambers through said ports, to cause said liquid to flow from one of said chambers to another one of said chambers. The pneumatic pressures may be selectively applied to transfer said liquid sequentially through more than two of said chambers.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Exemplary embodiments of the present invention utilize pneumatic pressures to selectively transfer liquids between inter-connected fluid chambers in a micro-fluidic device. The chambers are connected to pneumatic ports through which pneumatic pressures may be selectively applied in individual chambers above the respective liquid level. The chambers may be interconnected through a connecting conduit that is at least partially positioned above the liquid levels in the chambers for preventing unintended liquid transfer between the chambers.

Figure 1:
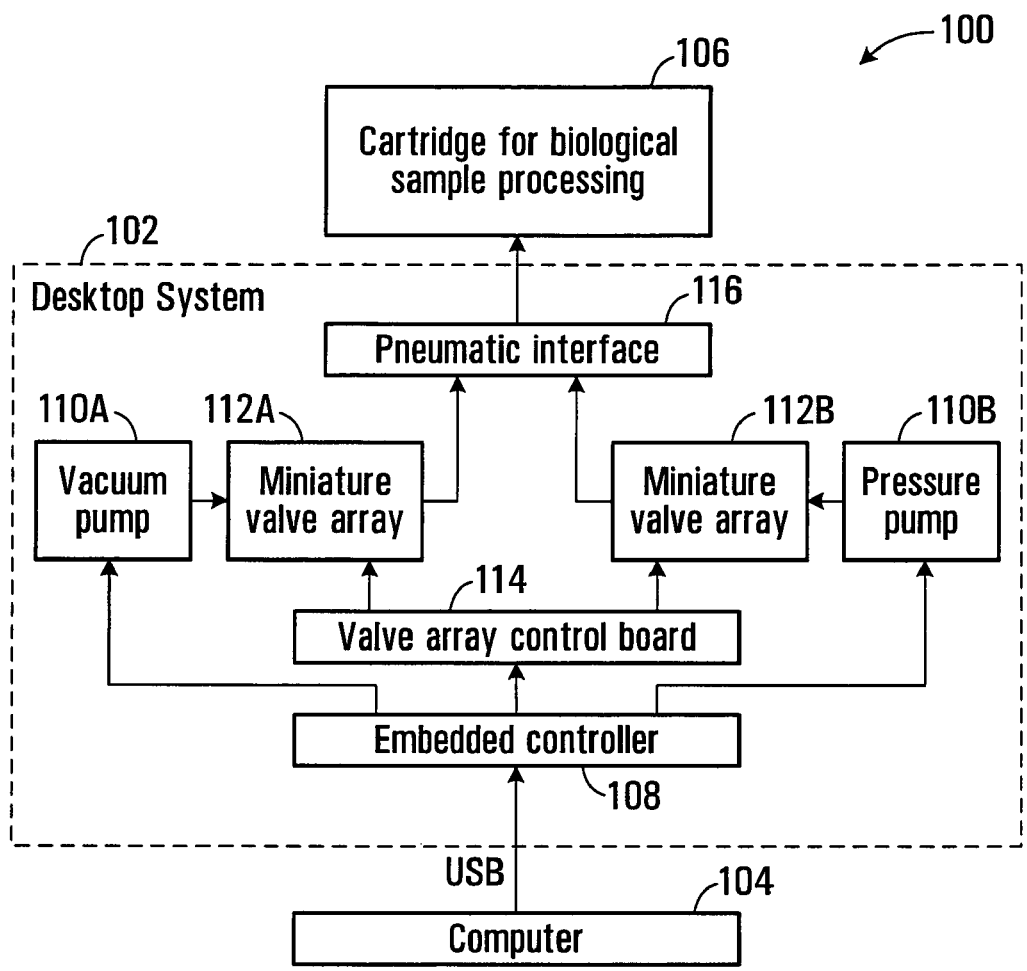
FIG. 1 is a block diagram of a fluidic apparatus, exemplary of an embodiment of the present invention.

FIG. 1 is a schematic block diagram showing a system 100 for processing fluidic biological samples, exemplary of an embodiment of the present invention.

System 100 includes station 102 which can be a desktop station. Station 102 is connected to a computer 104 and can receive a cartridge 106, as will be further detailed below.

Station 102 also includes an embedded controller 108, which communicates with computer 104, such as through a USB connection. Computer 104 may be a specially designed computer or a general-purpose computer loaded with specially designed program for control the operation of system 100.

Station 102 also includes a plurality of pumps 110A and 110B (also collectively and individually referred to as pump 110), miniature valve arrays 112A and 112B (also collectively and individually referred to as valve array or valve 112) and a valve array control board 114. One of the pumps, such as pump 110A, is a vacuum pump; another pump, such as pump 110B, is a pressure pump. The pumps may be miniature pumps, such as syringe pumps or peristaltic pumps. In some embodiments, the flow rate provided by the pumps may be from about 0.01 to about 50 ml/min. In other embodiments, the flow rate may be different. The valves may be miniature electromagnetic valves. The pumps may be air pumps. However, in different applications, different gas or fluid pumps may be used. In different embodiments, a pump 110 may be replaced with another pneumatic source, which may be an external vacuum or pressure source. In some cases, the atmosphere may provide a suitable pneumatic source.

Controller 108 is adapted and configured to control the operation of pumps 110 and valve arrays 112 through valve array control board 114. Controller 108 may include a microcontroller unit such as a PIC ("Programmable Intelligent Computer) microcontroller, or a programmable logic controller such as an Omron programmable logic controller, or the like.

Valves 112 are connected to a pneumatic interface 116. Valves 112 may include miniature valves available from SMC™, or pinch valves available from Cole-Parmer™, or other commercially available or specially designed valves.

Figure 2:
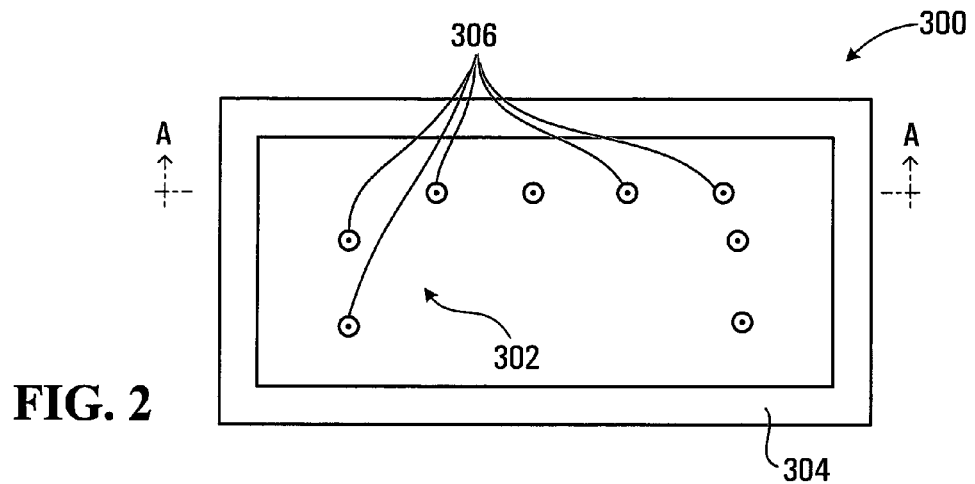
FIG. 2 is a top plan view of a receptacle base for use in the apparatus of FIG. 1.
Figure 3:
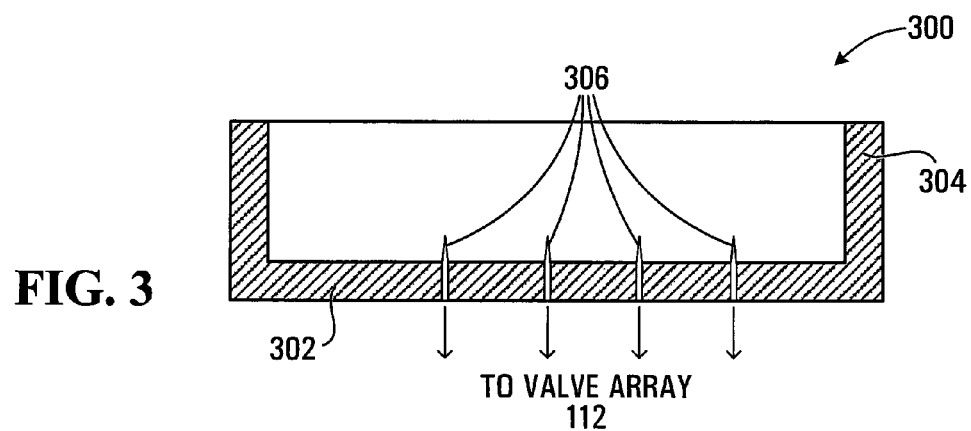
FIG. 3 is a cross-sectional elevation view of the base of FIG. 2 along the line A-A.

Interface 116 may include a receptacle/coupling unit or base 300 illustrated in FIGS. 2 and 3. Base 300 includes a base portion 302 and a wall portion 304 shaped for coupling with cartridge 106. A number of pneumatic conduits, in this case needles 306, extend upwardly from and through base portion 302. Each needle 306 has an internal conduit and is connected to a different valve in the valve array 112 for transferring a fluid through the valve 112 and the needle 306.

An exemplary cartridge 106 is shown in FIGS. 4 to 10, exemplary of an embodiment of the present invention.

Figure 4:
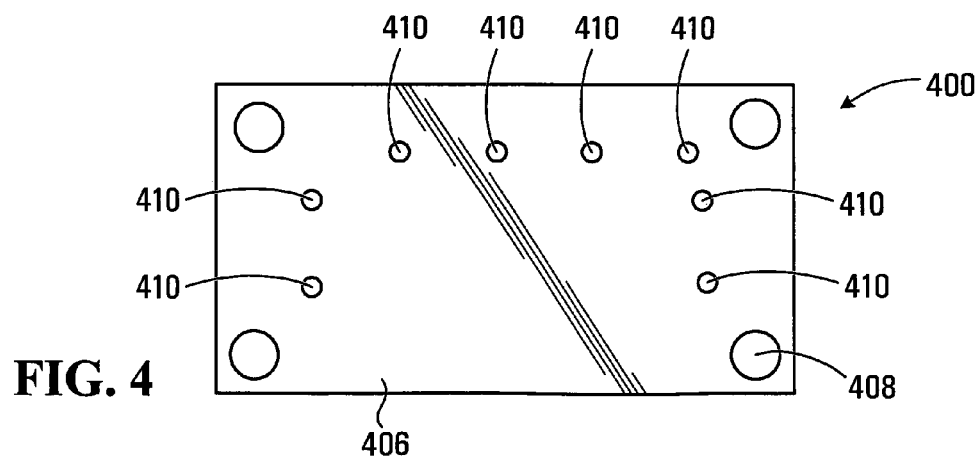
FIG. 4 is a bottom, see-through perspective view of a cartridge for use in the apparatus of FIG. 1, exemplary of an embodiment of the present invention.
Figure 5:
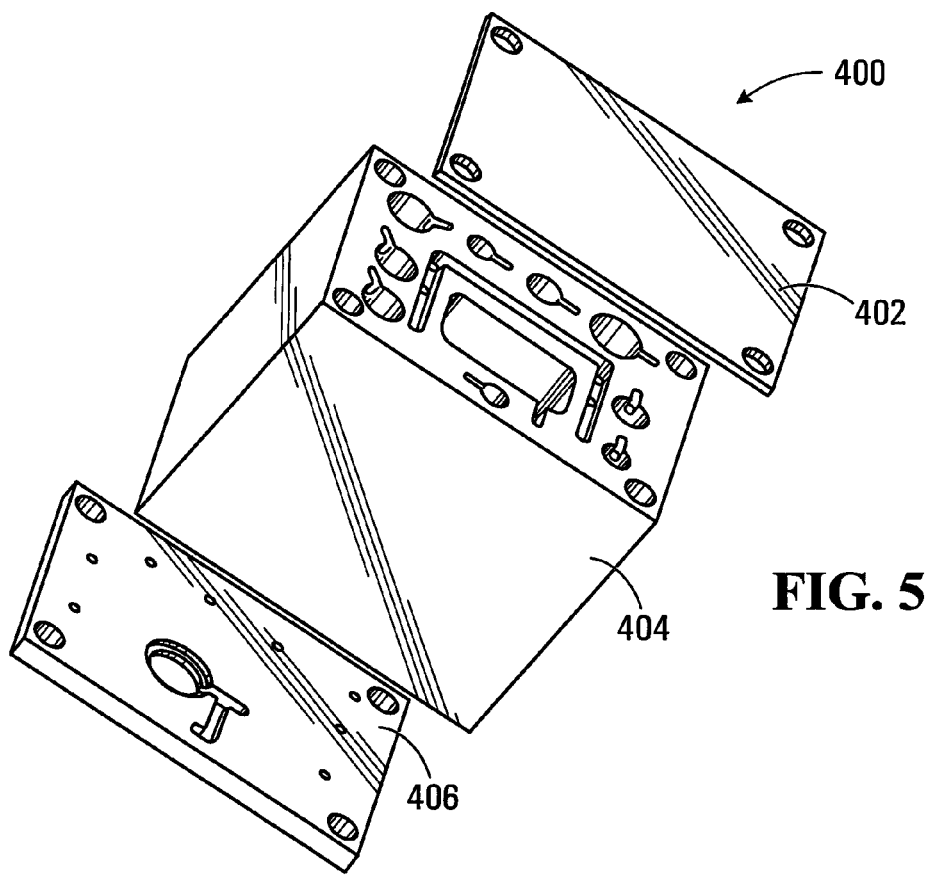
FIG. 5 is a top exploded perspective view of the cartridge of FIG. 4.
Figure 6:
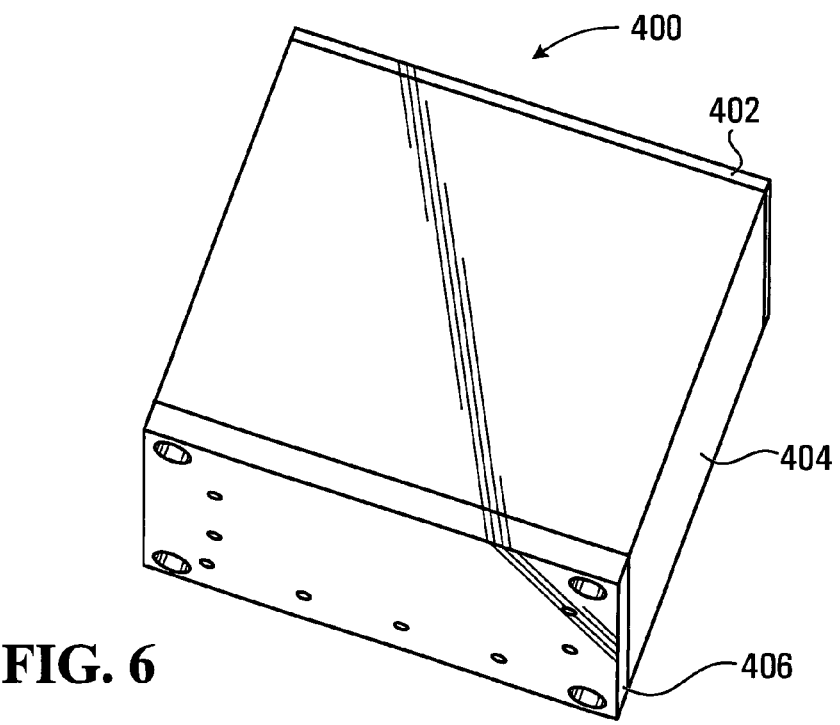
FIG. 6 is a bottom plan view of the cartridge of FIG. 4.
Figure 7:
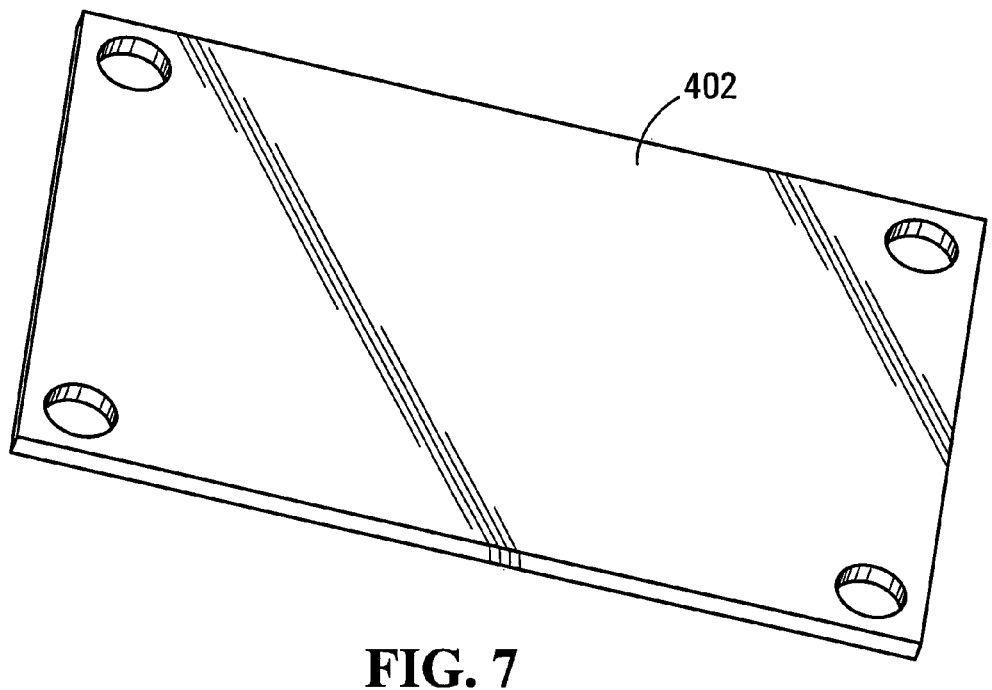
FIG. 7 is a top perspective view of the top portion of the cartridge of FIG. 4.

As shown in FIGS. 4, 5 and 6, the cartridge body 400 is formed of three portions, a top portion 402, a middle portion 404, and a bottom portion 406. The three portions may be separate portions and the middle portion 404 is sandwiched between top and bottom portions 402 and 406. The three portions 402, 404, 406 may be affixed together in any suitable manner. For example, the portions may be bolted together using bolts and nuts (not shown) or glued together using an adhesive. In some embodiments, it may be convenient to removably mount the top and bottom portions to the middle portion. For example, as illustrated in FIGS. 4 to 10, bolt holes 408 may be provided for securing the portions together.

As shown in FIG. 5, top portion 402 may be shaped as a flat plate with bolt holes 408. Alternatively, top portion 402 may be formed of a thin film or sheet such as a plastic tape which has an adhesive side. For example, the adhesive side of the tape may have a glue layer on its surface.

Figure 8:
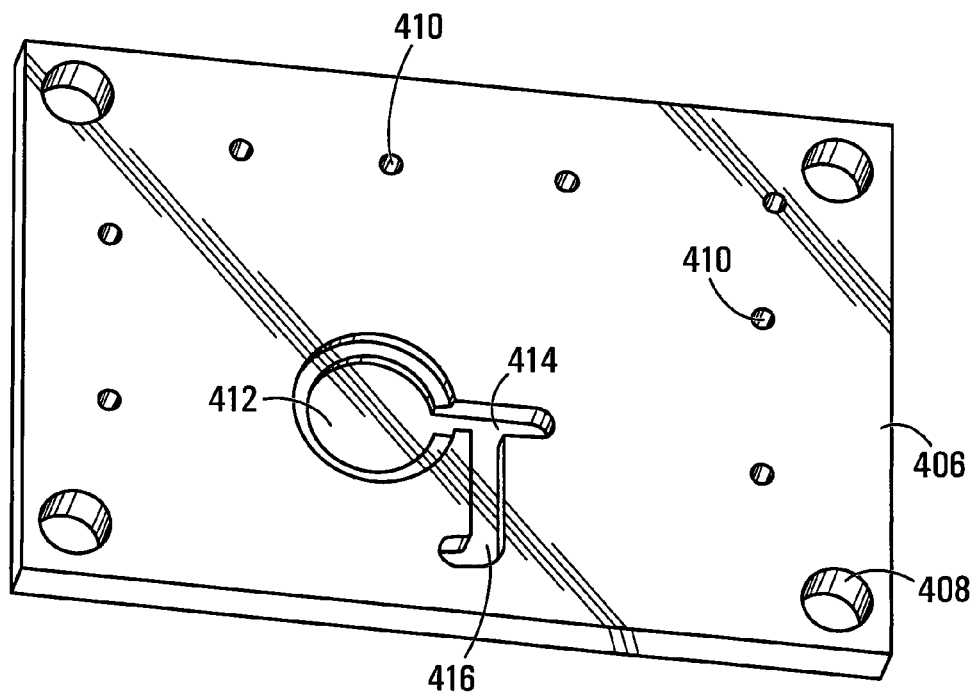
FIG. 8 is a bottom perspective view of the bottom portion of the cartridge of FIG. 4.

As shown in FIGS. 6 and 8, bottom portion 406 may be generally plate-shaped but provided with bolt holes 408, pneumatic ports 410 sealed with breakable seals 411 (not shown but see FIG. 11), a well 412, and fluid conduits or channels 414 and 416. Seals 411 may be formed of an adhesive tape. Pneumatic ports 410 may be sealed using the adhesive tape. Alternatively, bottom portion 406 may also be formed of a flat sheet such as a plastic sheet with an adhesive side that faces middle portion 404. Each port 410 is shaped to couple to a pneumatic conduit, such as needle 306, through seal 411.

Figure 9:
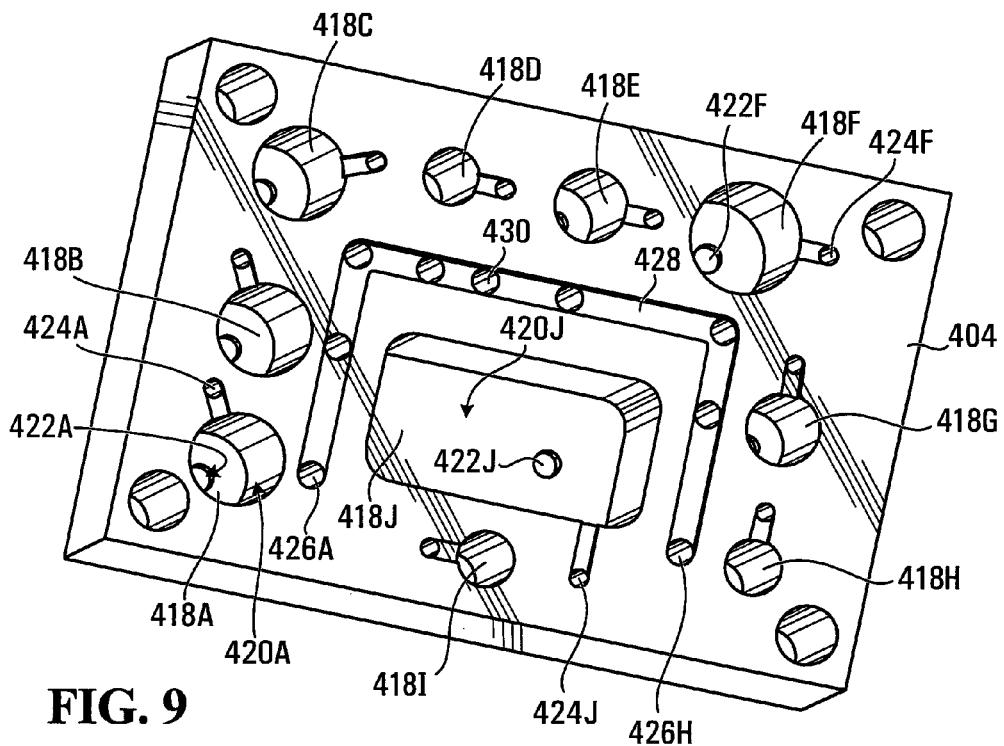
FIG. 9 is a top plan view of the middle portion of the cartridge of FIG. 4.
Figure 10:
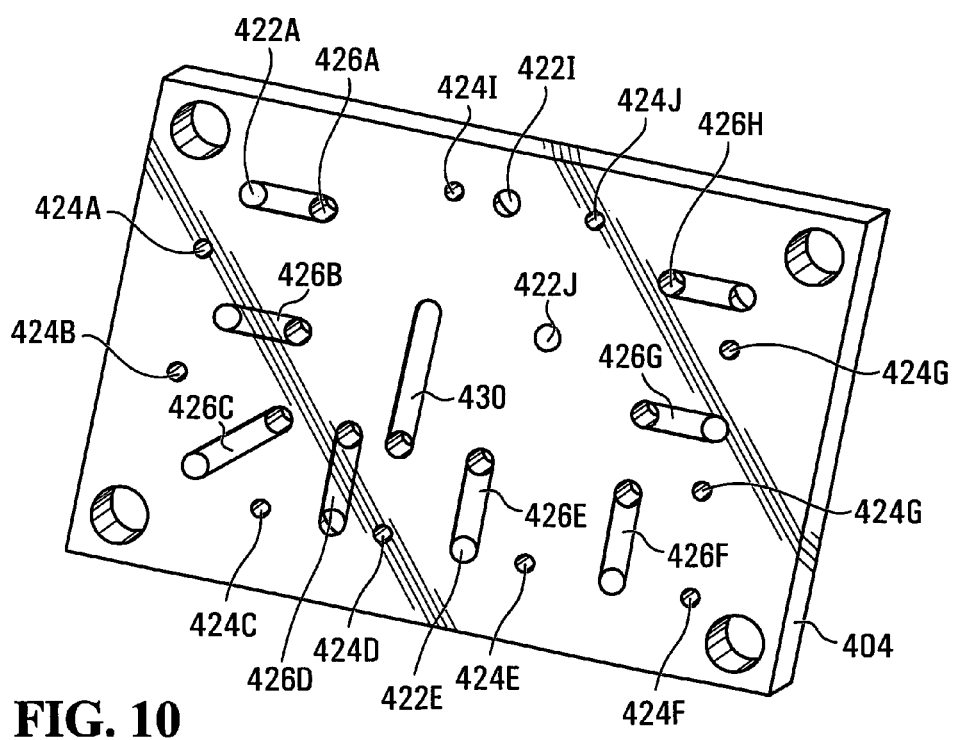
FIG. 10 is a bottom plan view of the middle portion of the cartridge of FIG. 4.

FIGS. 9 and 10 are top and bottom views of the middle portion 404 respectively. As shown, middle portion 404 defines a number of chambers 418A, 418B, 418C, 418D, 418E, 418F, 418G, 418H, 418I, and 418J (also collectively and individually referred to as chamber 418A). Each chamber 418 has a top opening 420 and a bottom opening 422 (for easy viewing, only 422A, 422B, 422G and 420J, and 422J are labeled in FIG. 9).

Each top opening 420 is connected with a pneumatic conduit or channel 424, which extends initially laterally and then downwardly to a respective pneumatic port 410 in bottom portion 406, so that the corresponding chamber 418 is in communication with the respective port 410 (for easy viewing, only channels 424A and 424J are labeled in FIG. 9 and FIG. 10).

Each bottom opening 422A to 422H is connected with a liquid conduit or channel 426 (labeled as 426A to 426H respectively), which extends initially laterally and then upwardly towards a top connecting conduit 428 that extends along the top surface of middle portion 404. Bottom openings 422I and 422J are connected to well 412 through conduits or channels 414 and 416 in the bottom portion 406. Well 412 is connected with a conduit or channel 430, which extends upwardly to connecting conduit 428.

Thus, chambers 418 are each in fluid communication with a respective port 410 through its top opening 420, and are in fluid communication with one another through their bottom openings 422 and connecting conduit 428.

When the three portions are affixed together such as with bolts and nuts or with an adhesive tape or thermo-diffusion bonding, the channels are tightly sealed and form closed fluid conduits for allowing fluid communication between the chambers and between the corresponding pairs of pneumatic ports and chambers. The contacting surfaces between portions 402 and 404, and between portions 404 and 406, may contain, or coated with, a sealing material. Well 412 when covered by bottom surface of middle portion 404 forms another fluid chamber, which may serve, for example, as a gene extraction chamber, as will be discussed further below. The chamber formed by well 412 is not connected directly to a pneumatic port, as it is not necessary to do so, as can be understood by persons skilled in the art.

As can be appreciated, cartridge body 400 initially defines a closed fluid network therein. Top and middle portions 402, 404 when affixed together define chambers 418 and top connecting conduit 428 therebetween. Top openings of chambers 418 are in fluid communication with corresponding ports 410. Bottom openings 420 of chambers 418 are in fluid communication with one another through connecting conduit 428.

Top openings 420 and connecting conduit 428 may be positioned at the same level, adjacent top portion 402, as illustrated in the figures. In different embodiments, connecting conduit 428 may be positioned higher or lower than top openings 420 but it should be at a level above the highest bottom opening 422 of the chambers 418 that are interconnected through connecting conduit 428 to prevent unintended transfer or mixing of the liquids contained in the chambers 418 through the connecting conduit 428. As can be appreciated, the allowable highest liquid level in the chambers 428 is dependent on the level of the highest section of the connecting conduit 428. Thus, a higher connecting conduit 428 (up to the top of the chambers) may be advantageous as it can allow more effective utilization of the chamber volume.

Figure 11:
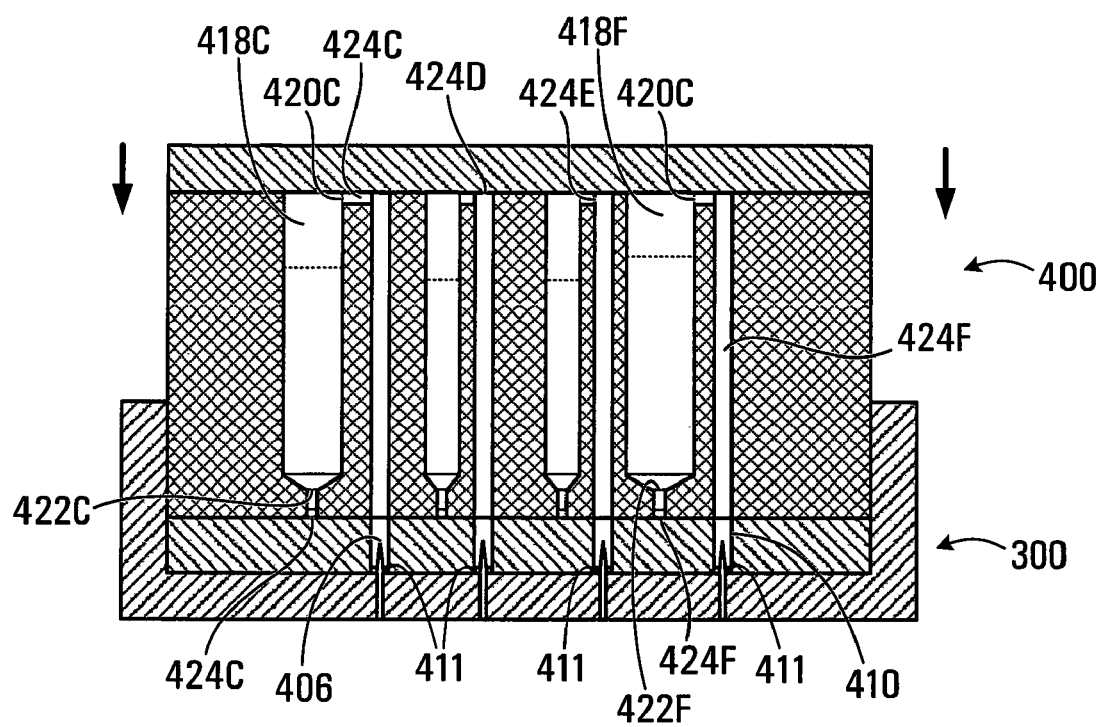
FIG. 11 is a cross-sectional elevation view of the base of FIG. 3 coupled to the cartridge of FIG. 4 in operation.

A chamber 418 may have a generally elongated cylindrical shape and a sloped bottom, and may extend vertically between top and bottom portions 402 and 406 (as better illustrated in FIG. 11). However, in different embodiments, chambers 418 may have a different cross-sectional shape and may be longer or shorter.

Cartridge body 400 or its portions may be formed using any suitable material. For example, each portion may be formed from a polymeric material, such as polycarbonate, poly(methyl methacrylate) (PMMA), or the like. Top portion 402 may be formed of a thin sealing material such as a plastic sheet with or without an adhesive surface. Seals 411 may be formed of any suitable sealing material such as a plastic film that can be conveniently broken with the needles 306. The plastic film may or may not have an adhesive layer on its surface.

The body 400 may be formed using traditional machining techniques, such as microinjection molding and computerized numerically controlled (CNC) machining, or using plastic injection molding, as can be understood by persons skilled in the art.

The internal surfaces of the chambers and channels may be cleaned or sterilized when desired or needed. In some cases, the internal surfaces of the chambers and channels may be coated with another polymer material, such as Teflon to modify the surface properties.

The sizes or dimensions of the cartridge 400 and the internal chambers 418, fluid conduits/channels, or openings may vary depending on the application. For biological applications, the sample amount is typically small, thus the fluidic chambers and channels may have dimensions on the order of micro-meters. When the dimensions are too large, it may be difficult to use pneumatic pressures to transfer small amounts of fluids. On the other hand, the dimensions should be large enough to allow sufficient transfer rate of the fluids under pneumatic pressures. In typical applications, the fluid channels and openings may have dimensions in the range of about 0.2 mm to about 1 mm. The chambers should have sufficient volumes for performing the particular desired process or treatment. Each chamber 418 or other fluid chambers may have a volume on the order of 1 micro liter to 100 milliliter.

The particular shapes of the openings, channels, conduits, and ports may very in different embodiments and depending on the application.

In use, one or more chambers 418 may be filled, such as being pre-loaded, with a liquid. The liquid may be a sample, a buffer, or a reagent liquid, or any other desired liquid. A chamber may also be used to store a product such as purified target genes, or to store wastes. Different chambers 418 may be initially loaded with different fluids.

The fluids may be loaded before covering the top surface of middle portion 404 with top portion 402. After loading the fluids, top portion 402 is attached and affixed to middle portion 404 to close and seal the exposed openings at the top of middle portion 404 and to prevent leakage or contamination during transportation or operation. In some embodiments, a fluid may be initially loaded into a chamber through a port 410 before the port 410 is sealed. However, in many applications, loading from the top with top portion 402 removed may be more convenient.

As illustrated in FIG. 11, when cartridge body 400 is coupled to base 300, seals 411 at ports 410 may be selectively broken by needles 306 which will pierce through the seals 411, thus establishing fluid communication between corresponding valves in valve array 112 and chambers 418, through ports 410, conduits 424 and top openings 420.

The valves in valve arrays 112A and 112B are each connected to a corresponding needle 306 and configured to selectively regulate a fluid flow through that needle 306. The pumps 110 are connected to the valve arrays 112A and 112B for selectively applying a positive or negative pressure to the ports 310 through values 112.

Computer 104 controls the operation of controller 108, which in turn controls the operation of pumps 110 and valves 112 to selectively apply pressured air (positive pressure) or vacuum (negative pressure) to ports 410, through needles 306. Depending on whether a positive or a negative pressure is applied at a port 410, a fluid may be selectively transferred to or from the corresponding chamber 418. If no change is needed for a particular chamber, the port for that chamber may remain closed, such as by closing the corresponding valve.

Figure 12:
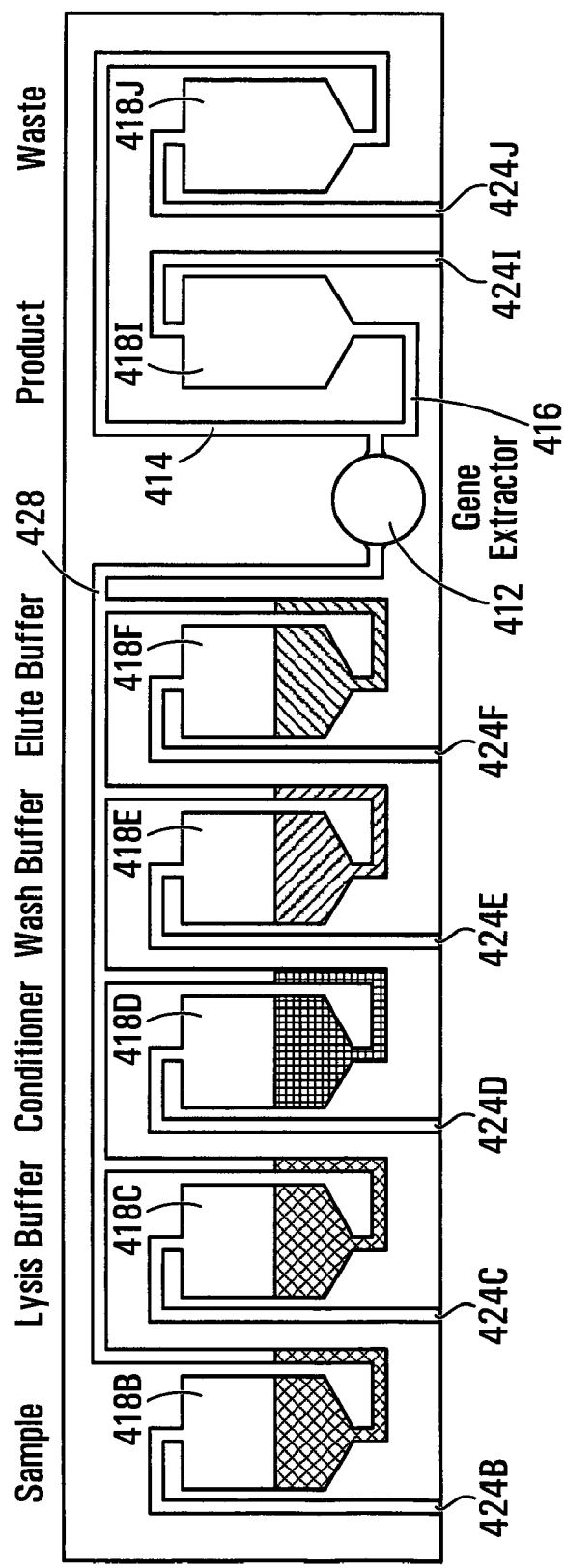
FIG. 12 is a schematic diagram of a part of the cartridge of FIG. 4 illustrating its operation, exemplary of an embodiment of the present invention.

For example, to perform gene extraction for PCR (polymerase chain reaction), cartridge 400 may be loaded with fluids as illustrated in FIG. 12, which schematically shows a similar cartridge with some modifications from cartridge 400. One modification is that some chambers are omitted in FIG. 12 as they are not used for this particular operation; further the bottom. Another modification is that bottom openings 424I and 424J are connected to connecting chamber 428 through gene extraction chamber 412, not directly. However, the operation procedure for transferring liquids between chambers 418B to 418F can be the same despite these changes. Assuming chambers 418B, 418C, 418D, 418E, 418F are loaded with sample, lysis buffer, conditioner, wash buffer, and elute buffer respectively. A gene extractor is deposited in well 412. The gene extractor may include a magnetic-based extractor, silica membrane, silica beads or another material that can attach to genes in a fluid with a high iron concentration. The genes may include DNA (Deoxyribonucleic acid), RNA (Ribonucleic acid), or mRNA (Messenger RNA). The gene extractor may be selected based on the particular genes to be extracted. Chambers 418I and 418J can be used for storing the product, extracted genes, and the waste produced by the reactions respectively. DNA or RNA degradation reagent may also be preloaded in one or more chambers.

In some cases, adjustment of the gene binding condition may be required. The buffers loaded in the chambers may include buffers for gene binding (such as pure or 70% ethanol) based on the target gene binding conditions.

In one embodiment, to perform sample lysing, the valves 112 corresponding to conduits 424D, 424E, 424F are closed. The valve 112B connected to conduit 424B is open and a pressurized gas such as air is supplied thereto, thus creating a positive pressure inside chamber 418B. The valve 112A connected to conduit 424C is open and a vacuum pressure is applied thereto, thus creating a negative pressure above the liquid in chamber 418C. The pressure differential thus drives sample liquid from chamber 418B to chamber 418C. Gas bubbles may also be created inside chamber 418C, facilitate mixing of the sample with the lysis buffer, after the sample liquid is completely transferred to chamber 418C. The sample may thus be mixed with the lysis buffer thoroughly to lyse the sample and to protect the genes from degradation.

A similar procedure may be used to transfer the lysed sample to chamber 418D to mix with the binding conditioner, thus adjusting the sample's gene condition.

The conditioned sample may be then transferred to well 412 directly or through one or more of chambers 418E and 418F, depending on the particular application as will be understood by those skilled in the art.

When magnetic beads are used as the gene extractor for gene extraction, the lysed sample may be mixed with the magnetic beads in well 412 using a similar procedure, without first going through the other chambers.

Gene extraction may also be performed in well 412 with the pre-treated sample fluid transferred from another chamber such as chamber 424D. The target genes in the sample will be attached to the gene extractor. The remaining liquid may be transferred to chamber 418J as waste.

Gene purification may be performed by transferring the wash buffer from chamber 424E to well 412. One wash buffer or different types of wash buffers may be used to wash the genes in multiple steps. If multiple wash buffers are used, two or more chambers may be allocated to store wash buffers. In one embodiment, wash buffer may be transferred from chamber 418E to chamber 418J, through well 412 and conduit 414. The waste may be later discharged from chamber 418J if the cartridge is to be recycled, or disposed with the cartridge.

Gene elution may be performed by transferring the elution buffer from chamber 418F to chamber 418I through well 412 and conduit 416. The elution buffer will release the genes attached to the gene extractor and carries the genes to chamber 418F. The target genes collected in chamber 418I may be withdrawn using pipette or syringe for downstream applications, such as gene amplification and detection. Extracted genes or other reaction products may be transferred to a detection chamber (not shown) for detection of certain signals or target. The detection chamber may be provided within cartridge 116 or may be provided in an external device (not shown) which can receive the material from cartridge 116.

Figure 13:
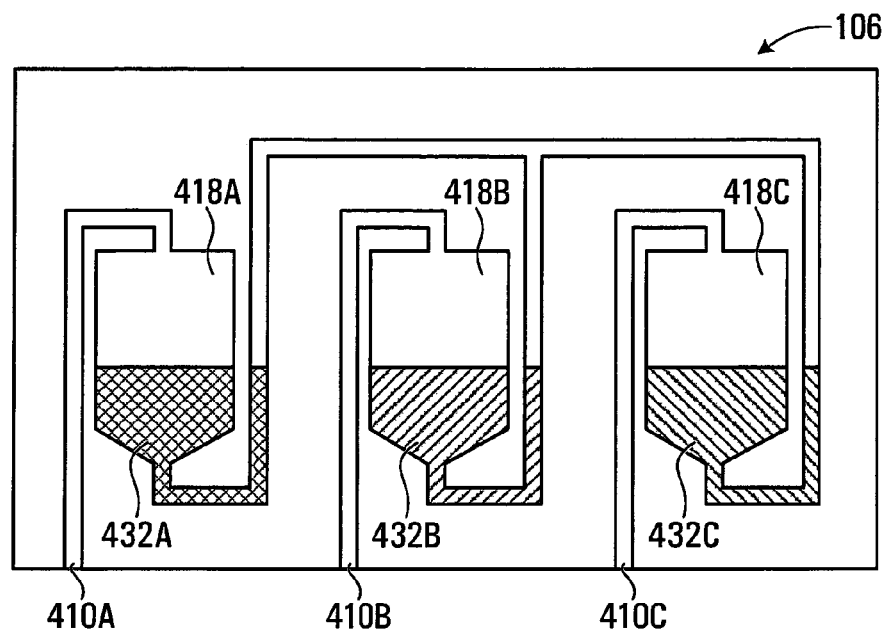
FIGS. 13, 14 and 15 are schematic diagrams of a part of the cartridge of FIG. 4 illustrating its operation, exemplary of an embodiment of the present invention.
Figure 14:
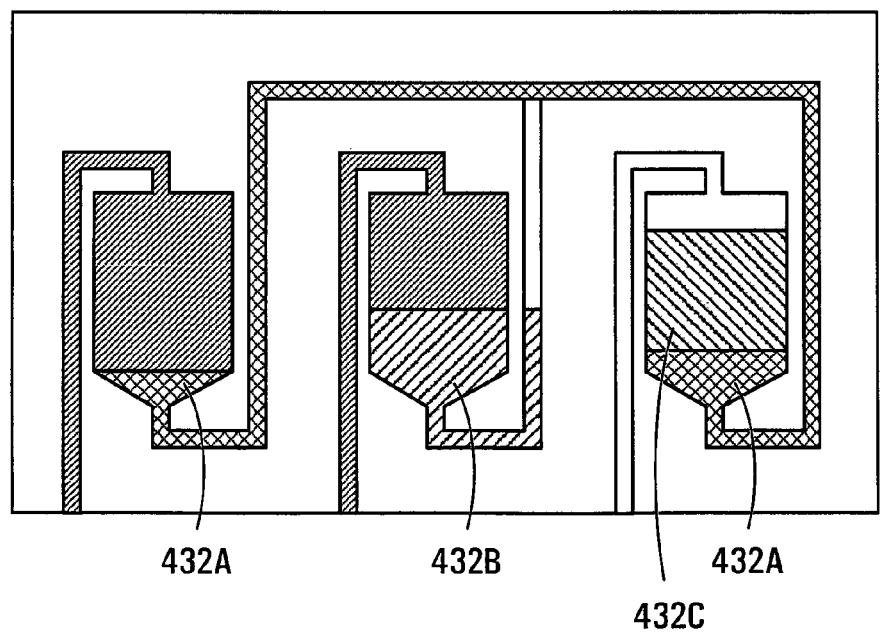
Figure 15:
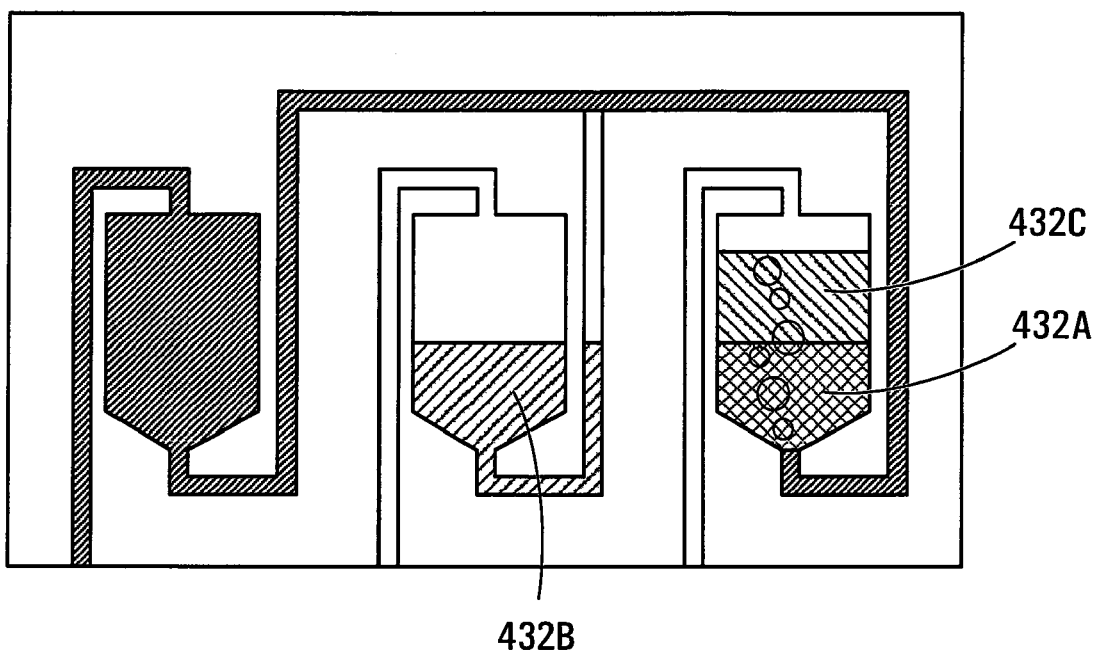

The operation of selectively transfer a fluid between the chambers is further illustrated with a simplified schematic diagram of the cartridge shown in FIGS. 13, 14 and 15. For simplicity, only three chambers are shown in these figures but it should be understood that more chambers may be operated in a similar manner.

As shown in FIG. 13, in an exemplary application, each of chambers 418A, 418B and 418C is filled with a liquid reagent 432A, 432B or 432C respectively. Ports 410A, 410B and 410C are initially sealed.

As shown in FIG. 14, in order to mix reagents 432A and 432C in chamber 418C, a positive gas (using air or another gas, such as an inert gas including $N_2$) pressure may be applied at port 410A and a vacuum pressure may be applied at port 410C, while port 410B may remain closed such as by closing the corresponding valve 112. The pneumatic pressure will drive reagent 432A through bottom opening 422A, connecting conduit 428 and bottom opening 420C into chamber 418C. Thus, reagents 432A and 432C can be brought into contact or mixed in chamber 418C. Due to the positive pressure within chamber 418B, reagent 432A is prevented from flowing into chamber 418B. The reagent in chamber 418A can be completely transferred to chamber 418C.

As shown in FIG. 15, reagent 432A may be completely transferred to chamber 418C, while reagent 432B remains in chamber 418B.

Because the connecting conduit 428 is above the liquid level in the chambers, and the pneumatic pressure is applied through the top opening, air can bubble through the liquids without driving the liquid out of the cartridge through the pneumatic ports. Conveniently, the air bubbles can be used to mix the reagents in the chambers such as in chamber 418C as shown in FIG. 15.

Conveniently, fluid transfer, mixing and processing may be effected without using any internal valves, pumps or other fluid regulating devices in the cartridge. The fluid transfer may be effected entirely by selectively applying pneumatic pressures to different ports. This process may be automated using computer 104 and controller 108. In some embodiments, the chambers may be interconnected such that a fluid may be transferred from any selected chamber to another selected chamber, or may be transferred sequentially from one to another through a series of chambers.

As can be understood, the exemplary cartridges described herein is simple in construction and can be made at relatively inexpensively. Since there is no moving parts in the cartridge it is very reliable. Since the sample and reagents can remain in a closed system during transportation and even during operation, the risk of contamination is significantly reduced.

The cartridge can also be conveniently configured and adapted for use in different applications, with different materials. Embodiments of the present invention can also be conveniently integrated with other systems such as a gene amplification unit or a gene detection unit.

Figure 16:
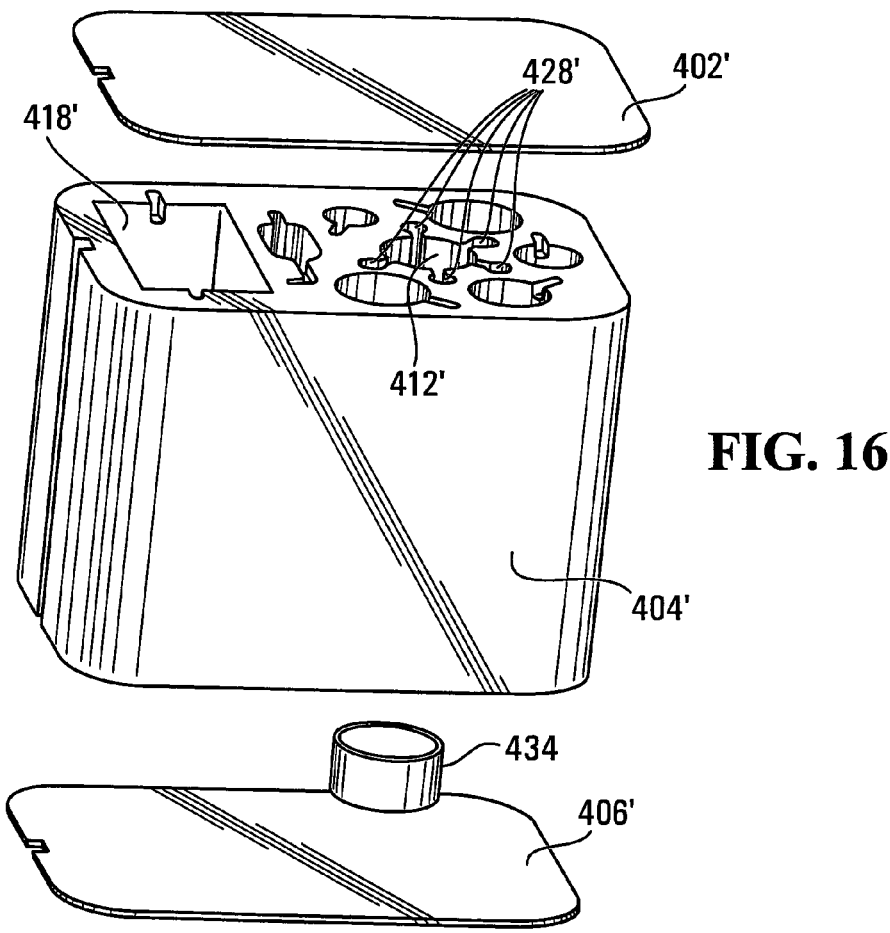
FIG. 16 is an exploded perspective view of an alternative cartridge, exemplary of an embodiment of the present invention.
Figure 17:
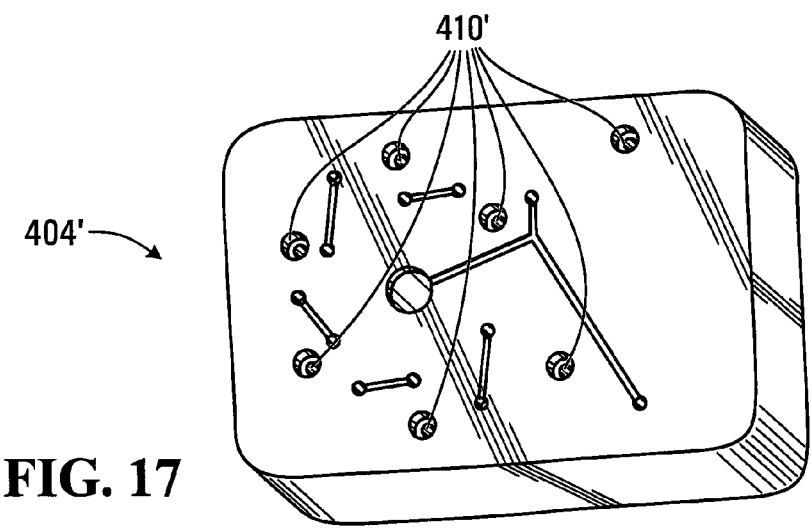
FIG. 17 is a bottom perspective view of the middle portion of the cartridge of FIG. 16.
Figure 18:
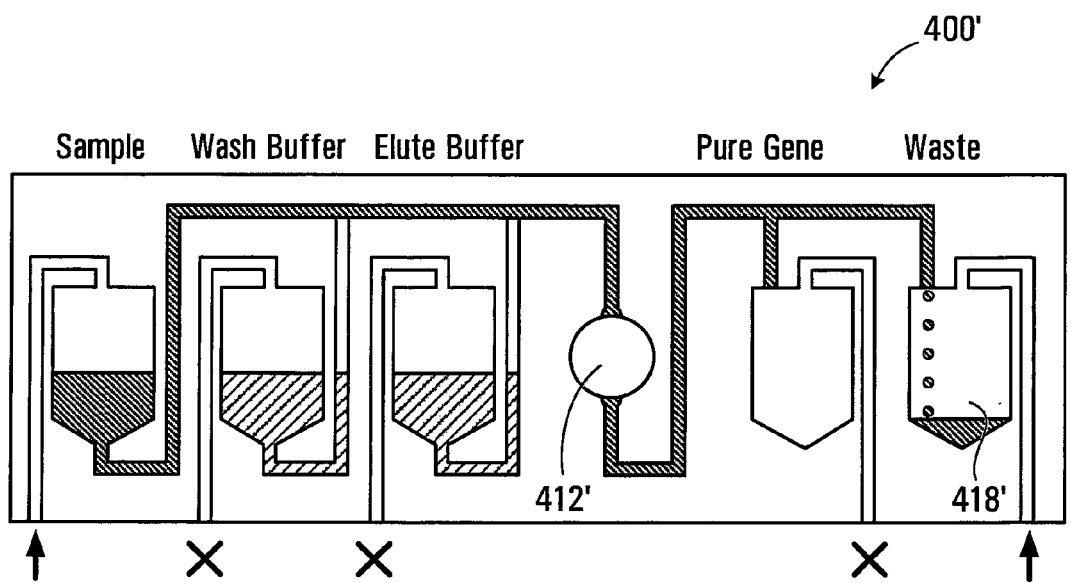
FIG. 18 is a schematic diagram of the alternative cartridge illustrating its operation, exemplary of an embodiment of the present invention.

In another embodiment, cartridge 116 may have an alternative construction, such as having a cartridge body 400' illustrated in FIGS. 16, 17 and 18. In cartridge body 400', processing chambers and channels are provided within middle portion 404'. Top and bottom portions 402' and 406' may be formed of flat sheets with no fluid channel or cavities. The flat sheets may have an adhesive surface, and may be formed of polymer tapes. The conduits and channel features may be entirely provided within the middle portion. The pneumatic ports 410' are also provided within middle portion 404' and are sealed by bottom portion 406'. Thus, bottom portion 406' serves as a seal in this embodiment.

Cartridge body 404' may define three or more chambers, which are used to initially receive a sample, a wash buffers and an elute buffer, respectively; a gene extractor chamber 412'; and two chambers for storing extracted and purified genes and wastes respectively during operation, as illustrated in FIGS. 16, 17 and 18. The chamber may be formed of through holes in middle portion 404'.

As better shown in FIGS. 16 and 18, the chambers in the alternative cartridge 400' may include a gene extractor chamber 412' and a waste chamber 418'. The remaining chambers shown may be used as reagent chambers for receiving samples and other reagent fluids or the extracted genes. A difference between the cartridges 400 and 400' is that the chambers for storing the waste and the product genes in cartridge 400' do not have a bottom opening but their top openings are connected to both the pneumatic ports and the extraction chamber 412'. As can be seen, a plurality of connecting conduits 428' are directly connected to the top opening of gene extractor chamber 412' in a radial arrangement, which are respectively connected to the other corresponding chambers. The other chambers, which have top and bottom openings similar to those described above with regard to body 400, are arranged around chamber 412'.

As illustrated, extractor chamber 412' is located at the center of middle portion 404' in the sense that other fluid chambers, except the waste chamber, are located around chamber 412'. A gene extractor 434, which may have a cup-shape, may be placed at the bottom of extractor chamber 412'.

During use, pre-loaded sample and washing buffers may be transferred, under pneumatic pressure, to gene extractor chamber 412' through channels 428'. A pre-loaded elute buffer may also be transferred to gene extractor chamber 412' to elute genes via channel 428'.

Figure 19:
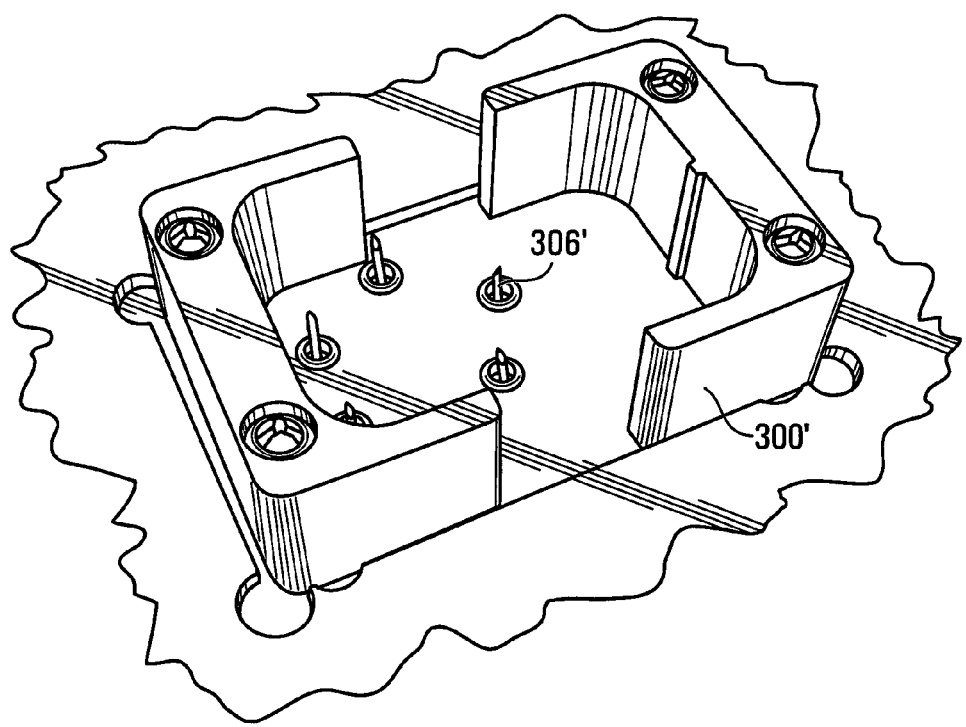
FIG. 19 is a perspective view of an alternative base suitable for coupling with the alternative cartridge.

For coupling to cartridge body 400', the receptacle base of the pneumatic interface 116 may be modified as shown in FIG. 19, so that modified base 300' can be properly coupled to the alternative cartridge 400' and the needles 306' are arranged to match the locations of the pneumatic ports 410' on the cartridge 400'. Needles 306' can thus pass through bottom portion 406' (acting as a seal) and communicate with pneumatic ports 410' when cartridge 400' is coupled to base 300'.

In use, the alternative cartridge 400' may be operated in a similar manner as described above with regard to cartridge body 400.

As can be understood, it is not necessary that the cartridge in an embodiment of the present invention to be provided with an internal integrated detector, or a detection window. Instead, the cartridge may be coupled to another unit that includes detectors and other detection devices. For this purpose, the body of the cartridge may be made of a material that is suitable for use with the particular detection method to be used. For example, the body may be made of a transparent material when an optical detection method is to be used, or a non-magnetic material when a magnetic probe is to be used.

As described above and shown in the figures, it is not necessary that every chamber in the cartridge is connected to a pneumatic port. The top and bottom openings of a chamber may be respectively connected to different connection channels or conduits.

Also as shown in FIGS. 11, 12 to 15, and 18, the bottom of a chamber may have a bottom surface that is sloped downwardly towards the bottom opening of the chamber. The bottom surface may be generally cone-shaped. Such a sloped bottom surface may be advantageous as the fluid in the chamber can be conveniently withdrawn through the bottom opening due to the gravitational force. In other words, the dead volume in the chamber is reduced or minimized with such a sloped bottom. While the bottom opening is shown to be located at the centre of the chamber in the figures, this is not necessary. The bottom opening may be relocated off centre. As long as the bottom opening is at the lowest level in the chamber and the bottom surface is sloped downwardly towards it, the same benefit may be obtained.

Of course, modification to the system and cartridge described herein is possible. For example, the cartridge body may have different constructions depending on the particular application. The shapes and number of chambers may vary. Each chamber may have more than one top or bottom openings. The top or bottom openings may be moved to the side wall of the chamber as long as they remain separated by a sufficient vertical distance to allow a sufficient amount of liquid to be received without losing liquid, or allow all liquid in the chamber be withdrawn through the bottom opening by applying pneumatic pressure.

As now can be understood, it is not necessary that the body of cartridge 106 is formed of three separate portions or layers. The cartridge may be formed from a single block of materials. However, layered construction may be convenient for manufacture and pre-loading of the fluids.

It is not necessary that the pneumatic ports 410 are located at the bottom portion of the cartridge body 400. The ports may be positioned elsewhere such as at the top or on the size of the body 400.

The top portion 402, the seals 411, or the bottom portion 406, may be removable and replaceable so that the cartridge 106 may be conveniently re-used.

Multiple connecting conduits 428 may be provided between different chambers. To isolate the liquids in different chambers, it my be sufficient that at least a portion of each connecting conduit 428 is at a level above the highest liquid level in the chambers 418 that are interconnected through that connecting conduit 428.

It is not necessary that the pump is provided within station 102. For example, when available, any compressed air supply or source may be used to apply positive air pressure to the ports. Any available vacuum source may also be used.

In the embodiments shown in the drawings, the cartridge 106 may include six to eleven fluid chambers. In different embodiments, the number of chambers may be different depending on the particular application. Further, it is not necessary that all the chambers are at the same level or that all chambers are inter-connected. For example, a chamber may be positioned above or higher than another chamber. It should be understood that the term "above" as used herein do not require that one chamber is directly above another chamber. It is sufficient if the bottom level of one chamber is at a higher level than the bottom level of the other chamber. Further, it should be understood that the terms "higher" or "lower" is used with the assumption that the cartridge body is placed in an upright position with the top portion on top.

While needles 306 and seals 411 may be conveniently used in some embodiments, particularly when the size of the ports are small, the pneumatic conduits and the coupling between a pneumatic port 410 and a pneumatic conduit for selectively applying a pneumatic pressure may be provided in different manners. For example, other types of coupling arrangements may be used in different embodiments.

In different embodiments, a different base station that is connectable to the cartridge 106 may be used for selectively applying pneumatic pressures to the chambers 418 through ports 410. The base station may include a base configured for coupling with the cartridge body 400, pneumatic conduits mounted on the base for coupling with ports 410 to selectively apply the pneumatic pressures through the seals 411. The base station may also include valves each connected to a pneumatic conduit for regulating the fluid flow therethrough. A controller may be provided for control the operation of the valves. Each pneumatic conduit may be connected to two valves, which are in turn connected to two different pressure devices, one for applying a first pneumatic pressure and the other for applying a second pneumatic pressure lower than the first pneumatic pressure, so that the difference in the pneumatic pressures is sufficient to cause fluid transfer between the chambers in the cartridge. The pressure devices may include pumps, a pressured gas (such as pressured air) line, or a vacuum line. The first pressure may be higher than one atmosphere and the second pressure may be lower than one atmosphere. In some embodiments, both pressures may be higher than one atmosphere. The pumps may be separately provided or integrated with the base station. The applied pressures and the valves may be automatically or manually controlled.

As now can be understood, the methods and apparatus described herein can be used to transfer and process raw biological materials that contain genes protein and reagents. After pre-treatment, the target genes or protein can be extracted using the same apparatus. Different raw biological materials can be processed using embodiments described herein, which include blood, cultured cells, serum, other types of body fluids, and the like. The target genes can be DNA, RNA, mRNA, protein, or the like.

Exemplary embodiments described herein can be used in various applications, including as part of a clinical or point-of-care disease diagnostics system, for sample preparation in research or clinical use, in forensic studies or sample processing, in the field of disease or medical research, in the field of chemistry or biological research such as molecular chemistry research, or in other similar fields.

Other features, benefits and advantages of the embodiments described herein not expressly mentioned above can be understood from this description and the drawings by those skilled in the art.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A micro-fluidic device, comprising:
   a body defining
      first, second and third pneumatic ports, each sealed with a seal and shaped to couple to a pneumatic conduit through said seal;
      a first chamber for receiving a first liquid, having a first top opening and a first bottom opening, said first top opening in fluid communication with said first port;
      a second chamber for receiving a second liquid, having a second top opening and a second bottom opening, said second top opening in fluid communication with said second port;
      a third chamber for receiving a third liquid, having a third top opening and a third bottom opening, said third top opening in fluid communication with said third port; and
      a connecting conduit above each one of said first, second and third bottom openings, said bottom openings in fluid communication with one another through said connecting conduit,
   wherein selective application of pneumatic pressures to said chambers through said pneumatic conduits transfers a liquid from one of said chambers to another one of said chambers through said connecting conduit.

2. The micro-fluidic device of claim 1, wherein each one of said chambers has a bottom surface sloped downwardly towards said bottom opening of said each chamber.

3. The micro-fluid device of claim 1, wherein at least a section of said connecting conduit is at a level above a liquid level in said chambers.

4. The micro-fluidic device of claim 1, wherein said body comprises a top portion, a bottom portion, and a middle portion, said chambers and connecting conduit defined by said middle and top portions.

5. The micro-fluidic device of claim 4, wherein at least a section of said connecting conduit is adjacent said top portion.

6. The micro-fluidic device of claim 4, wherein said top openings of said chambers are adjacent said top portion.

7. The micro-fluidic device of claim 4, wherein said ports are defined by said bottom portion.

8. The micro-fluidic device of claim 4, wherein said middle portion defines a first conduit extending between said first port and said first top opening, a second conduit extending between said second port and said second top opening, and a third conduit extending between said third port and said third top opening.

9. The micro-fluidic device of claim 8, wherein said middle portion defines a fourth conduit extending between said first bottom opening and said connecting conduit, a fifth conduit extending between said second bottom opening and said connecting conduit, and a sixth conduit extending between said third bottom opening and said connecting conduit.

10. The micro-fluidic device of claim 4, wherein said top, middle and bottom portions are separate portions, said middle portion being sandwiched between said top and bottom portions.

11. The micro-fluidic device of claim 10, wherein at least one of said top and bottom portions is formed of a flat sheet.

12. The micro-fluidic device of claim 4, wherein at least one of said top portion and said bottom portion is made of a plastic material.

13. The micro-fluidic device of claim 1, wherein said body defines more than three inter-connected chambers.

14. The micro-fluidic device of claim 13, wherein said body defines six to eleven inter-connected chambers.

15. The micro-fluidic device of claim 1, wherein said liquid comprises a reagent, a buffer, a sample, or a gene binding conditioner.

16. The micro-fluidic device of claim 1, wherein at least two of said chambers contain different liquids.

17. The micro-fluidic device of claim 1, wherein at least a portion of said body is made of a polymer.

18. The micro-fluidic device of claim 17, wherein said polymer comprises polycarbonate or poly(methyl methacrylate).

19. The micro-fluidic device of claim 1, wherein said seal is made of a plastic material.

20. The micro-fluidic device of claim 1, wherein said body defines a gene extractor chamber, said gene extractor chamber containing a gene extractor and being in fluid communication with said connecting conduit.

21. The micro-fluidic device of claim 20, wherein said body defines a product chamber and a waste chamber, each in fluid communication with said gene extractor chamber.

22. The micro-fluidic device of claim 1, wherein said device is a cartridge.

23. The micro-fluidic device of claim 1, wherein said pneumatic conduit comprises a needle.

24. An apparatus comprising a device as defined in claim 1, and a station connectable to said device for selectively applying pneumatic pressures to said chambers through said ports of said device.

25. The apparatus of claim 24, wherein said station comprises:
a base configured for coupling with said device,
a plurality of pneumatic conduits mounted on said base, shaped to couple to said ports through said seals when said device is coupled to said base, and
a plurality of valves each connected to one of said pneumatic conduits for selectively regulating a fluid flow through said pneumatic conduits.

26. The apparatus of claim 25, wherein a first set of said plurality of valves are connected to a first pressure device for selectively applying to said ports a first pneumatic pressure, and a second set of said plurality of valves are connected to a second pressure device selectively applying to said ports a second pneumatic pressure lower than said first pneumatic pressure.

27. The apparatus of claim 26, wherein said first pneumatic pressure is higher than one atmosphere, and said second pneumatic pressure is lower than one atmosphere.

28. The apparatus of claim 27, wherein said first pressure device comprises a pressure pump, and said second pressure device comprises a vacuum pump.

29. The apparatus of claim 26, wherein said station comprises a controller for controlling operation of said valves and said pressure devices.

30. The apparatus of claim 29, wherein said station comprises a computer in communication with said controller for controlling operation of said controller.

31. A method of operating the device of claim 1, wherein at least one of said chambers contains said liquid, comprising:
coupling said pneumatic conduits to said ports;
selectively applying different pneumatic pressures to said chambers through said ports, to cause said liquid to flow from one of said chambers to another one of said chambers.

32. The method of claim 31, comprising selectively applying said pneumatic pressures to transfer said liquid sequentially through more than two of said chambers.

* * * * *